United States Patent [19]

Cuscurida et al.

[11] Patent Number: 5,103,062
[45] Date of Patent: Apr. 7, 1992

[54] MODIFIED NORMALLY LIQUID, WATER-SOLUBLE POLYOXYALKYLENE POLYAMINES

[75] Inventors: Michael Cuscurida; Ernest L. Yeakey, both of Austin, Tex.

[73] Assignee: Texaco Inc., White Plains, N.Y.

[21] Appl. No.: 36,955

[22] Filed: Apr. 10, 1987

[51] Int. Cl.⁵ .......................................... C07C 209/16
[52] U.S. Cl. ................................. 564/479; 564/474; 564/505
[58] Field of Search ...................... 564/474, 479, 505

[56] References Cited

U.S. PATENT DOCUMENTS

| | | | |
|---|---|---|---|
| 2,174,761 | 10/1939 | Schuette et al. | 260/458 |
| 2,425,845 | 8/1947 | Toussaint et al. | 260/615 |
| 2,674,619 | 4/1954 | Lundsted | 260/485 |
| 3,535,307 | 10/1970 | Moss et al. | 260/209 |
| 3,654,370 | 4/1972 | Yeakey | 564/505 |
| 3,706,714 | 12/1972 | Lloyd et al. | 260/77.5 |
| 3,838,076 | 9/1974 | Moss et al. | 260/2.5 |
| 4,021,384 | 5/1977 | Brader et al. | 260/2.5 |
| 4,181,682 | 1/1980 | Watts, Jr. et al. | 564/505 |
| 4,186,254 | 1/1980 | Cuscurida et al. | 521/115 |
| 4,243,760 | 1/1981 | McDaniel et al. | 521/176 |
| 4,273,884 | 6/1981 | Dominguez | 521/114 |
| 4,316,991 | 2/1982 | Speranza et al. | 568/609 |
| 4,528,112 | 7/1985 | Speranza et al. | 252/182 |
| 4,535,133 | 8/1985 | Cuscurida et al. | 525/504 |
| 4,535,189 | 8/1985 | Cuscurida | 568/620 |

FOREIGN PATENT DOCUMENTS

| | | | |
|---|---|---|---|
| 1033912 | 6/1966 | United Kingdom | 564/505 |
| 2171711 | 9/1986 | United Kingdom | 564/474 |

OTHER PUBLICATIONS

Jefferson Chemical Co., Inc., "Polyethylene Glycols", Technical Brochure, 1967.
Texaco Chemical Company, "Our Chemical Products", 1981.
Texaco Chemical Company, "JEFFAMINE Polyoxypropyleneamine Curing Agents for Epoxy Resins", 1978, 1986.
Wyandotte Chemicals, "The Pluronic Grid", Fourth Edition, before 1985.
Texaco Chemical Company, "Epoxy Curing Agents and Accelerators", before 1985.
Texaco Chemical Company, "THANOL PPG-2000 Polyol", 1981.
Texaco Chemical Company, "THANOL F-3000 Polyol", 1982.
Texaco Chemical Company, "FEFFAMINE Poly(oxyethylene)diamines, JEFFAMINE ED Compounds", 1985.

*Primary Examiner*—Richard L. Raymond
*Assistant Examiner*—Scott C. Rand
*Attorney, Agent, or Firm*—Jack H. Park; Kenneth R. Priem; Carl G. Ries

[57] ABSTRACT

In accordance with the process of the present invention normally liquid, water-soluble poly(oxyethylene/oxypropylene) polyamine products are prepared using an initiator, which may contain oxyethylene groups. In a series of alkoxylation reaction steps the initiator is reacted with predetermined weight percentages of ethylene oxide and propylene oxide, said process comprising the steps of:

a. Charging a predetermined percentage of initiator to an alkoxylation reaction zone,
b. Alkoxylating said initiator therein with predetermined percentages of ethylene oxide and propylene oxide to provide an intermediate polyol,
c. Propoxylating said intermediate polyol with a predetermined percentage of propylene oxide to provide a normally liquid, water-soluble precursor polyol, and
d. Catalytically reductively aminating said precursor polyol in the presence of a reductive amination catalyst in a reaction zone under reductive amination conditions in the presence of ammonia and hydrogen to provide said water-soluble poly(oxyethylene/oxypropylene) polyamine product.

14 Claims, No Drawings

MODIFIED NORMALLY LIQUID, WATER-SOLUBLE POLYOXYALKYLENE POLYAMINES

BACKGROUND OF THE INVENTION

1. Field of the Invention

This invention relates to modified normally liquid, water-soluble polyoxyalkylene polyamines and to a process by which they may be prepared. More particularly, this invention relates to normally liquid, water-soluble polyoxyethylene polyamines modified by the inclusion of oxypropylene groups and to a special process to be used in preparing the modified polyamines.

Still more particularly, this invention is directed to normally liquid, water-soluble poly(oxyethylene/oxypropylene)polyamine products having an average molecular weight of about 1000 to about 8000 and a functionality of about 2 to about 4 which are prepared by adding predetermined amounts of ethylene oxide and propylene oxide to an alkoxylation susceptible polyhydric alcohol initiator to form an intermediate which is then propoxylated to form a precursor polyol which, in turn, is reductively aminated in the presence of a hydrogenation/dehydrogenation catalyst to provide the desired normally liquid, water-soluble poly(oxyethylene/oxypropylene) polyamine.

The poly(oxyethylene/oxypropylene) polyamine may be used to form an aqueous solution containing from about 1 to about 50 wt.% of the polyamine. The aqueous solution of the polyamine may be used as such, e.g., as a major component of a functional fluid such as a hydraulic fluid, or as a feedstock for a further chemical processing step.

The poly(oxyethylene/oxypropylene) precursor polyols of the present invention are also water soluble liquids at ambient temperatures and may be used as feedstocks for the preparation of the poly(oxyethylene/oxypropylene) polyamines of the present invention or may be used to prepare aqueous solutions of the poly(oxyethylene/oxypropylene) polyol containing from about 1 to about 50 wt.% of the polyol.

2. Prior Art

Yeakey U.S. Pat. No. 3,654,370 discloses a process for the preparation of polyoxyalkylene polyamines by the reaction of a polyoxyalkylene polyol feedstock with ammonia in the presence of hydrogen under reductive amination conditions to provide the corresponding polyoxyalkylene polyamine.

Lee et al. U.S. Pat. No. 3,236,895 discloses a process for producing polyoxyalkylene polyamines such as polyoxyalkylene diamines by reacting a polyoxyalkylene diol with ammonia in the presence of hydrogen.

British Patent No. 934,636 also discloses the preparation of oxyalkylene amines by reacting polyoxyalkylene glycol ethers with ammonia using a hydrogenation/dehydrogenation catalyst.

Boettger et al. U.S. Pat. No. 4,014,933 discloses the reaction of alcohols with ammonia at elevated temperatures and pressures in the presence of hydrogen and a hydrogenation catalyst.

Nickel/copper/chromia catalysts of the type preferred by Yeakey are disclosed in Moss U. S. Patent No. 3,152,998.

SUMMARY OF THE INVENTION

1. Background of the Invention

It is known that polyoxyethylene polyols have good water solubility characteristics. Therefore, it has been proposed in the past to ethoxylate alkoxylation susceptible initiator alcohols containing 2 to 4 hydroxyl groups and to reductively aminate the resultant polyoxyethylene polyol in order to provide water soluble products useful as epoxy curing agents, and also useful in the preparation of polyurea RIM elastomers, polyamides and functional fluids. For many applications it is desirable to use a comparatively high molecular weight material having a molecular weight of about 1000 to about 8000. However, typical polyoxyethylene polyols within this molecular weight range are normally solid materials which are processed with difficulty. Thus, unless special precautions are taken during the processing of the polyol, it can solidify or otherwise plug or interfere with the processing operations being conducted.

Another class of raw materials that are frequently prepared are polyoxypropylene polyols. The polyoxypropylene polyols are characterized, in general, by water insolubility and therefore their use is not favored in situations wherein water solubility is a desired characteristic.

It has been surprisingly discovered in accordance with the present invention that polyoxyethylene polyamines which are normally liquid at ambient temperatures of about 30° C., such as temperatures of 30°–35° C. and which have good watersolubility characteristics can be prepared by incorporating from about 20 to about 40 wt.% of propylene oxide into the polyoxyethylene polyol molecule in a special manner.

2. General Description

In accordance with the present invention normally liquid, water-soluble poly(oxyethylene/oxypropylene) polyamine products having an average molecular weight of about 1000 to about 8000 and a functionality of about 2 to 4 are provided. The poly(oxyethylene/oxypropylene) polyol precursors, used as feedstocks for the reductive amination step are also characterized by being normally liquid and watersoluble.

In order to obtain polyol precursors and polyamine products having the desired water solubility characteristics, it is necessary that a particular processing sequence be followed.

In accordance with the process of the present invention an initiator, which may contain oxyethylene groups, ethylene oxide and propylene oxide are charged to a reaction zone in a series of alkoxylation reaction steps with predetermined weight percentages of initiator, ethylene oxide and/or propylene oxide being charged for each step, based on the total weight of all of the initiator ethylene oxide and propylene oxide charged during all of the steps of the process. The alkoxylation reaction steps are conducted under basic alkoxylation conditions under substantially anhydrous conditions.

The initiator comprises an oxyalkylation susceptible polyhydric alcohol having 2 to 4 hydroxyl groups and a molecular weight of about 200 to about 1000 which, optionally, will comprise oxyethylene groups and will constitute about 10 to about 60% of the total molecular weight of the water soluble poly(oxyethylene/oxypropylene) polyamine product.

The processing sequence comprises the steps of:

a. Charging a predetermined percentage of the initiator to an alkoxylation reaction zone, b. Alkoxylating said initiator in said alkoxylation reaction zone with predetermined percentages of ethylene oxide and propylene oxide to provide an intermediate polyol, c. Propoxylating the intermediate polyol in the alkoxylation reaction zone with a predetermined percentage of propylene oxide to provide a precursor polyol, and d. Catalytically reductively aminating the precursor polyol in the presence of a reductive amination catalyst in a reaction zone under reductive amination conditions in the presence of ammonia and hydrogen to provide the desired water soluble poly(oxyethylene/oxypropylene) polyamine product.

The predetermined percentages, when the initiator contains all oxyethylene groups are in the ranges of:

|  | Minimum Weight Percent of | | Maximum Weight Percent of | |
| --- | --- | --- | --- | --- |
|  | Initiator + Ethylene Oxide | Propylene Oxide | Initiator + Ethylene Oxide | Propylene Oxide |
| Intermediate | 60 | 15 | 80 | 25 |
| Precursor Polyol | 60 | 20 | 80 | 40 |

When the initiator does not contain oxyethylene groups, the predetermined percentages are in the ranges of:

|  | Minimum Weight Percent of | | Maximum Weight Percent of | |
| --- | --- | --- | --- | --- |
|  | Initiator + Ethylene Oxide | Propylene Oxide | Initiator + Ethylene Oxide | Propylene Oxide |
| Initiator plus Intermediate | 80 | 15 | 60 | 25 |
| Precursor Polyol | 80 | 20 | 60 | 40 |

In alkoxylating the initiator in order to prepare the intermediate polyol, the ethylene oxide and propylene oxide may be premixed before the alkoxylation to form a heteropolymer or the ethylene oxide and propylene oxide may be separately added to the alkoxylation reaction zone.

A preferred class of polyamines of the present invention are prepared by alkoxylating a polyoxyethylene glycol initiator having an average molecular weight of about 200 to about 1000 with a predetermined amount of a mixture of ethylene oxide and propylene oxide to provide a poly(oxyethylene/oxypropylene) heteropolymer polyol intermediate which, in turn, is propoxylated to provide a poly(oxyethylene/oxypropylene) diol precursor for the reductive amination step.

DETAILED DESCRIPTION

As indicated earlier, the starting materials for the present invention are an alkoxylation susceptible polyhydric alcohol containing 2 to 4 hydroxyl groups having an average molecular weight of about 200 to about 1000 and propylene oxide and ethylene oxide.

Hydrogen and ammonia are used in the processing sequence and a hydrogenation/dehydrogenation catalyst is used for the reductive amination step.

THE INITIATOR

The initiators to be used in accordance with the present invention are oxyalkylation susceptible polyhydric alcohols containing 2 to 4 hydroxyl groups, having an average molecular weight of about 200 to about 1000. Examples of such initiators include ethylene glycol, diethylene glycol, triethylene glycol, poly(oxyethylene) glycols, propylene glycol, dipropylene glycol, polypropylene glycol, 1,2,6-hexane triol, trimethylolethane, trimethylolpropane, glycerine, pentaerythritol and alpha methyl glucoside.

A preferred class of initiators are the polyoxyethylene glycols having a molecular weight of about 200 to about 1000, such as a molecular weight of about 600.

THE INTERMEDIATE POLYOL

In accordance with the present invention, the initiator is reacted with a predetermined amount of ethylene oxide and propylene oxide in an alkoxylation reaction zone in order to provide an intermediate polyol.

The alkoxylation is conducted in a conventional fashion, for example, by adding the propylene oxide and ethylene oxide to a kettle containing the initiator. The alkoxylation is conducted under basic conditions.

Suitable alkoxylation conditions include, for example, the use of temperatures within the range of about 75° to about 150° C. and pressures within the range of about 10 to about 100 psig. A base, such as an alkali metal or alkaline earth metal catalyst should be present in order to promote the alkoxylation and is used in an amount of about 0.25 to about 5.0 wt.%, based on the weight of the initiator (see, for example, Cuscurida et al. U.S. Pat. No. 3,535,307 and U.S. Pat. No. 4,316,991).

In the preparation of the intermediate polyol, the propylene oxide and ethylene oxide are preferably added to the alkoxylation zone in admixture in order to provide an intermediate polyol which is a poly(oxyethylene/oxypropylene) heteropolymer polyol. However, if desired, the initiator may be reacted first with a predetermined amount of ethylene oxide and then with the predetermined amount of propylene oxide or, first with the predetermined amount of propylene oxide and then with the predetermined amount of ethylene oxide in order to provide block copolymer polyoxyethylene polyoxypropylene polyols.

THE PRECURSOR POLYOL

In accordance with the present invention an initiator is reacted with a mixture of propylene oxide and ethylene oxide containing predetermined amounts of ethylene oxide and propylene oxide, as described herein, to form an intermediate polyol which is capped with a predetermined amount of propylene oxide to provide a precursor polyol for use as a feedstock for the reductive amination step.

The predetermined weight percentages of ethylene oxide and propylene oxide to be used when the initiator contains oxyethylene groups is given in the following table:

|  | Minimum Weight Percent of | | Maximum Weight Percent of | |
| --- | --- | --- | --- | --- |
|  | Initiator + Ethylene Oxide | Propylene Oxide | Initiator + Ethylene Oxide | Propylene Oxide |
| Intermediate | 60 | 15 | 80 | 25 |
| Precursor Polyol | 60 | 20 | 80 | 40 |

Note from the table that the final precursor polyol will contain from about 60 to about 80 wt.% of oxyethylene groups and, correspondingly, from about 40 to about 20 wt.% of oxypropylene groups. It will also be noted from the table, under the column heading of "Minimum Weight Percent of", that 15/20 wt.% or 75% of the predetermined weight percentage of propylene oxide was added to the intermediate polyol and, under the column heading of "Maximum Weight Percent of", that 24/40 wt.%, or about 62.5% of the predetermined weight percentage of propylene oxide was added to the intermediate polyol.

It is not necessary that the initiator be an oxyethylene containing initiator and when the initiator does not contain oxyethylene groups, the percentages of ethylene oxide and propylene oxide to be used are given in the following table:

|  | Minimum Weight Percent of | | Maximum Weight Percent of | |
| --- | --- | --- | --- | --- |
|  | Initiator + Ethylene Oxide | Propylene Oxide | Initiator + Ethylene Oxide | Propylene Oxide |
| Initiator plus Intermediate | 80 | 15 | 60 | 25 |
| Precursor Polyol | 80 | 20 | 60 | 40 |

REDUCTIVE AMINATION OF THE PRECURSOR POLYOL

The precursor polyol after being neutralized with any suitable acid or chemical adsorbent, such as for example, oxalic acid or magnesium silicate, and filtered for the removal of insoluble materials is charged to a reductive amination zone where it is brought into contact with a reductive amination catalyst, frequently referred to as a hydrogenation-dehydrogenation catalyst, in the presence of ammonia and hydrogen under reductive amination conditions. Such conditions may include, for example, a temperature from within the range of about 150° to about 275° C. and a pressure within the range of about 500 to about 5000 psig with temperatures within the range of about 180° to 240° C. and pressures within the range of about 1500 to about 3000 psig being preferred.

Any suitable hydrogenation catalyst may be used, such as a catalyst comprising one or more of the metals of group VIIIB of the Periodic Table, such as iron, cobalt, nickel, ruthenium, rhodium, palladium, platinum, mixed with one or more metals of group VIB of the Periodic Table such as chromium, molybdenum or tungsten. A promoter from group IB of the Periodic Table, such as copper, may also be included. As an example, a catalyst may be used comprising from about 60 to about 85 mole percent of nickel, about 14 to about 37 mole percent of copper and about 1 to about 5 mole percent of chromium (as chromia), such as a catalyst of the type disclosed in Moss U.S. Pat. No. 3,152,998. As another example, a catalyst of the type disclosed in Boettger et al. U.S. Pat. No. 4,014,933 may be used containing from about 70 to about 95 wt.% of a mixture of cobalt and nickel and from about 5 to about 30 wt.% of iron. As another example, a catalyst of the type disclosed in Habermann U.S. Pat. No. 4,152,353 may be used, such as a catalyst comprising nickel, copper and a third component which may be iron, zinc, zirconium or a mixture thereof, e.g., a catalyst containing from about 20 to about 49 wt.% of nickel, about 36 to about 79 wt.% of copper and about 1 to about 15 wt.% of iron, zinc, zirconium or a mixture thereof.

The reductive amination is preferably conducted on a continuous basis with the precursor polyol, ammonia and hydrogen being continuously charged to a reactor containing a fixed bed of catalyst and with the reaction product being continually withdrawn.

The reaction product is suitably depressured so as to recover excess hydrogen and ammonia for recycle and is then fractionated to remove byproduct water of reaction and to provide the desired poly(oxyethylene/oxypropylene) polyamine product.

In conducting the reductive amination, the reductive amination conditions to be utilized may suitably include the use of from about 4 to about 150 moles of ammonia per hydroxyl equivalent of feedstock. Hydrogen is preferably used in an amount ranging from about 0.5 to about 10 mole equivalents of hydrogen per hydroxyl equivalent of feedstock. The contact times within the reaction zone, when the reaction is conducted on a batch basis, may suitably be within the range of from about 0.1 to about 6 hours and more preferably from about 0.15 to about 2 hours.

When the reaction is conducted on a continuous basis using catalyst pellets, reaction times may suitably be from about 0.1 to about 2 grams of feedstock per hour per cubic centimeter of catalyst and, more preferably, from about 0.3 to about 1.6 grams of feedstock per hour per cubic centimeter of catalyst.

Also, the reductive amination may be conducted in the presence of about 1 to about 200 moles of ammonia per mole of precursor polyol and more preferably, from about 4 to about 130 moles of ammonia per mole of precursor polyol. From about 0.1 to about 50 moles of hydrogen per mole of precursor polyol may be employed and, more preferably, from about 1 to about 25 moles of hydrogen per mole of precursor polyol.

The molecular weight of the polyol is determined by the number of moles of epoxide that are reacted with the alcohol initiator. Since the addition is random, the final alkoxylation product will not be a pure compound but, rather, will be a mixture of poly(oxyethylene/oxypropylene) polyols. For example, if the precursor polyol has an average molecular weight of about 1000, it will actually be composed of a mixture of poly(oxyethylene/oxypropylene) polyols having molecular weights varying from about 800 to about 1200, the molecular weight distribution following a Gaussian distribution curve. As the molecular weight of the precursor polyol increases, the spread of the molecular weights will also increase. Thus, when the average molecular weight is about 3000, the deviation will be about ±400 molecular weight units so that most of the product will fall within the range of molecular weights ranging from about 2600 to about 3400.

As the molecular weight is still further increased, the percentage of deviation will increase still further. For example, a 5000 molecular weight poly(oxyethylene/oxypropylene) precursor polyol will have a molecular weight distribution of about ±1000 so that the actual molecular weight range will be from about 4000 to about 6000. Again, the molecular weight distribution will tend to follow a Gaussian distribution curve.

SPECIFIC EXAMPLES

The invention will be further illustrated by the following specific examples which are given by way of illustration and not as limitations on the scope of this invention.

EXAMPLE 1

Research Notebook 6158-27; Preparation of Polyoxyalkyleneamines Precursor Polyol Into a ten-gallon kettle were charged 7 lb of a 600 m.w. polyethylene glycol (PEG 600) and 35.2g 45% aqueous potassium hydroxide. The reactor was then purged with prepurified nitrogen. Maintaining a nitrogen purge, the reactor was heated to 100° C. and stripped to a water content of less than 0.1%. A mixture of 12.4 lb propylene oxide (PO) and 54.9 lb of ethylene oxide (EO) was then reacted at 115°-120° C. at 50 psig. Approximately 7.0 hours were required for addition of the mixed oxides. The reaction mixture was then digested 1.7 hours to an equilibrium pressure. PO (8.3 lb) was then reacted at 120° C. and 50 psig over a 0.75 hour period. After digestion to an equilibrium pressure, the alkaline polyol was neutralized at 95° C. by stirring two hours with 141g magnesium silicate which was added as an aqueous slurry. Di-t-butyl p-cresol (37.6g) was added to stabilize the product. The neutralized product was then vacuum stripped to a minimum pressure, nitrogen stripped and filtered. The finished product had the following properties:

| Run no. | 6158-27 |
|---|---|
| Properties | |
| Acid no.; mg KOH/g | 0.003 |
| Hydroxyl no. mg/KOH/g | 17.6 |
| Water, wt. % | 0.007 |
| Unsaturation, meq/g | 0.032 |
| pH in 10:6 isopropanol-water | 8.2 |
| Color, Pt-Co | 50 |
| Sodium, ppm | 0.2 |
| Potassium, ppm | 1.3 |
| Peroxide, ppm | 2.0 |
| Viscosity, 100° F. cs | 2508 |
| PO/EO | 25.8/74.2 |
| Melting point, °C. | 33 |
| Water solubility | Yes |

The product was a liquid at 30°-35° C. and readily dissolved in water at room temperature and was used to form a 33 wt.% solution in water.

The percentages of initiator, propylene oxide and ethylene oxide in the intermediate polyol and the precursor polyol were calculated as follows:

| Component | Amount, lbs. |
|---|---|
| PEG 600 | 7 |
| Mixed PO | 12.4 |
| Mixed EO | 54.9 |
| cap PO | 8.3 |

Percent EO in intermediate polyol equals $$\frac{\text{initiator} + \text{mixed } EO}{\text{initiator} + \text{mixed } EO + \text{mixed } PO} \times 100 = \frac{61.9}{74.3} \times 100 = 83.3\%$$

Percent PO in intermediate polyol equals $$\frac{\text{mixed } PO}{\text{initiator} + \text{mixed } EO + \text{mixed } PO} \times 100 = \frac{12.4}{60} \times 100 = 16.7\%$$

Percent EO in precursor polyol equals $$\frac{\text{initiator} + \text{mixed } EO}{\text{initiator} + \text{mixed } EO + \text{mixed } PO + \text{cap } PO} \times 100 =$$

$$\frac{61.9}{82.6} \times 100 = 74.9\%$$

Percent PO in precursor polyol equals $$\frac{\text{mixed } PO + \text{cap } PO}{\text{initiator} + \text{mixed } EO + \text{mixed } PO + \text{cap } PO} \times 100 =$$

$$\frac{20.7}{82.6} \times 100 = 25\%$$

EXAMPLE 2

This example will illustrate the preparation of a prior art water soluble 5500 m.w. diol.

Into a 125-gallon kettle was charged 123 lbs of a 750 m.w. polyoxyethylene glycol which had an alkalinity of 5 mg KOH/g. The reactor was then purged with nitrogen and stripped while heating to 130° C. EO (770 lb) was then reacted at 125°-130° C. at 50 psig. The reaction mixture was circulated through an exchanger after the first 50 lb of EO had been added. Since the product freezes in the 50°-60° C. range it was necessary to maintain positive flow through the exchanger continuously and to keep the process lines heated. After digestion to an equilibrium pressure, the reactor was vented to a flare. PO (52 lb) was then reacted at 125°-130° C. and 50 psig. After digestion to an equilibrium pressure, the alkaline material was neutralized with 205g oxalic acid dihydrate to a pH of 7.5. An aqueous slurry of 181g magnesium silicate was then added to the product and digested an additional hour at 95°-100° C. Di-t-butyl p-cresol (53g) and Celite 545 filter aid (2 lb) were then added to the neutralized product. The product was then vacuum stripped to a minimum pressure at 110° C., nitrogen stripped, and filtered. The finished product had the following properties:

| Acid no., mg KOH/g | 0.03 |
|---|---|
| Hydroxyl no., mg KOH/g | 20.4 |
| Water, wt. % | 0.03 |
| pH in 10:6 isopropanol-water | 6.0 |
| Sodium, ppm | 2.3 |
| Potassium, ppm | 0.7 |
| Melting point, °C. | 48 |
| Water solubility | Yes |

Although the product had good water solubility, it had an undesirably high melting point.

EXAMPLE 3

The polyether diol of Example 1 was reductively aminated in a 1250 ml reactor using the following reaction conditions: (See U.S. Pat. No. 3,654,370)

| Polyol feed rate, lb/hr | 0.5 |
|---|---|
| Ammonia feed rate, lb/hr | 1.0 |
| Hydrogen feed rate, l/hr | 25 |
| Temperature, °C. | 201 |
| Reactor pressure, psig | 2000 |
| Catalyst | Proprietary copper, chromium, nickel |

The ammonia, polyol, and hydrogen were fed into the reactor through heated feed lines. The product was collected at atmospheric pressure at 70° C. Crude product was then stripped on a rotary evaporator at 99–100 psig and 5 mm Hg. Properties of the stripped product were as follows:

| | |
|---|---|
| Total acetylatables, meq/g | 0.36 |
| Total amine, meq/g | 0.27 |
| Primary amine, meq/g | 0.26 |
| Melting point, °C. | 20 |
| Water solubility | Yes |

Reductive amination of the polyether diol of Example 2 yielded a product having the following properties:

| | |
|---|---|
| Total acetylatables, meq/g | 0.315 |
| Total amine, meq/g | 0.27 |
| Primary amine, meq/g | 0.26 |
| Melting point, °C | 49 |
| Water solubility | Yes |

EXAMPLE 4

This example will illustrate the preparation of a 2150 m.w. polyol of this invention.

Into a 10-gallon kettle were charged 20 lb of a 600 m.w. polyethylene glycol and 30g 45% aqueous potassium hydroxide. The reactor was then purged with prepurified nitrogen. Maintaining a nitrogen purge the reactor was heated to 100° C. The initiator was then dried to a water content of less than 0.1% by using vacuum and nitrogen stripping. A mixture of 13.4 lb PO and 26.6 lb EO was then reacted at 120°–125° C. at 50 psig. Approximately five hours was required for addition of the mixed oxides. After digestion to an equilibrium pressure, the polyol was capped by reaction with 6.6 lb PO at 120°–125° C. at 50 psig. After digestion to an equilibrium pressure, the alkaline product was neutralized at 95° C. by stirring two hours with 120g magnesium silicate which was added as an aqueous slurry. Di-t-butyl p-cresol (30.2g) was then added to stabilize the product. The neutralized product was then vacuum stripped to a minimum pressure, nitrogen stripped, and filtered. The finished product was a liquid at room temperature (77° F.) which had the following properties:

| | |
|---|---|
| Acid no., mg KOH/g | 0.003 |
| Hydroxyl no., mg KOH/g | 52.2 |
| Water, wt. % | 0.03 |
| Unsaturation, meq/g | 0.005 |
| pH in 10:6 isopropanol-water | 7.7 |
| Color, Pt—Co | 45 |
| Sodium, ppm | 0.2 |
| Potassium, ppm | 0.2 |
| Peroxides, ppm | 1.44 |
| Viscosity, °F., cs | |
| 77° | 442 |
| 100° | 235 |
| PO/EO | 29.5/70.5 |

The polyol of this Example 4 was used to make a 50 wt.% aqueous solution.

The percentages of initiator, propylene oxide and ethylene oxide in the intermediate polyol and the precursor polyol were calculated as follows:

| Component | Amount, lbs. |
|---|---|
| PEG 600 | 20 |
| Mixed PO | 13.4 |
| Mixed EO | 26.6 |
| cap PO | 6.6 |

Percent EO in intermediate polyol equals $$\frac{\text{initiator} + \text{mixed } EO}{\text{initiator} + \text{mixed } EO + \text{mixed } PO} \times 100 = \frac{46.6}{60} \times 100 = 77.7\%$$

PO in intermediate polyol equals $$\frac{\text{mixed } PO}{\text{initiator} + \text{mixed } EO + \text{mixed } PO} \times 100 = \frac{13.4}{60} \times 100 = 22.3\%$$

Percent $EO$ in precursor polyol equals $$\frac{\text{initiator} + \text{mixed } EO}{\text{initiator} + \text{mixed } EO + \text{mixed } PO + \text{cap } PO} \times 100 =$$

$$\frac{46.6}{66.6} \times 100 = 70\%$$

Percent $PO$ in precursor polyol equals $$\frac{\text{mixed } PO + \text{cap } PO}{\text{initiator} + \text{mixed } EO + \text{mixed } PO + \text{cap } PO} \times 100 =$$

$$\frac{20}{66.6} \times 100 = 30\%$$

EXAMPLE 5

This example will illustrate the preparation of a prior art water soluble 2000 m.w. diol.

Into a 125-gallon kettle was charged 315 lb of a 700 m.w. polyethylene glycol which had an alkalinity of 5 mg KOH/g. The reactor was then purged with nitrogen and stripped while heating to 130° C. Ethylene oxide (494 lb) was then reacted at 125°–130° C. at 50 psig. The reaction mixture was circulated through an exchanger during EO addition. Since the product freezes in the 42°–45° C. range it was necessary to maintain positive flow through the exchanger continuously and to keep the process lines heated. After digestion to an equilibrium pressure, the reactor was vented to a flare. PO (91 lb) was then reacted at 125°–130° C. at 50 psig. After digestion to an equilibrium pressure, the alkaline material was neutralized with 635g oxalic acid dihydrate to a pH of 7.5 Di-t-butyl p=cresol (104g) and Celite (2 lb) were then added to the neutralized product. The product was then vacuum stripped to a minimum pressure, nitrogen stripped, and filtered. The finished product had the following properties:

| | |
|---|---|
| Acid no., mg KOH/g | 0.027 |
| Hydroxyl no., mg KOH/g | 56.9 |
| Water, wt. % | 0.2 |
| pH in 10:6 isopropanol-water | 6.8 |
| Sodium, ppm | 0.04 |
| Potassium, ppm | 7.3 |
| Color, Pt—Co | >50 |
| Melting point, °C. | 43.95 |
| Water solubility | Yes |

EXAMPLE 6

The polyol of Example 4 was reductively aminated using Ni-2715 catalyst. Best results were obtained at 200° C. and a total space velocity of 0.88 g/cc cat/hr.

The resultant product was a liquid at room temperature. Its properties were as follows:

| Total acetylatables, meq/g | 0.95 |
|---|---|
| Total amine, meq/g | 0.85 |
| Primary amine, meg/q | 0.84 |
| Water, wt. % | 0.01 |
| Viscosity, 77° F., cs | 354 |
| Melting point, °C. | Liquid at room temperature |
| Water solubility | Yes |

Reductive amination of the prior art 2000 m.w. diol of Example 5 formed a liquid product which had the following properties:

| Total acetylatables, meq/g | 0.96 |
|---|---|
| Total amine, meq/g | 0.90 |
| Primary amine, meg/q | 0.87 |
| Melting point, °C. | 40.5 |
| Water solubility | Yes |

EXAMPLES 7 AND 8

Two additional water-soluble precursor polyols were prepared using a polyethylene glycol having an average molecular weight of 600 as an initiator. The procedure used was essentially that described in Example 1, the materials were used in the following reaction sequence:

Example 7—Polyoxyethylene glycol (600 m.w.) plus a mixture of 107 moles EO/18.3 moles PO plus 12.3 moles PO;

Example 8—Polyoxyethylene glycol initiator (average molecular weight 600) plus a mixture of 18.1 moles EO with 6.9 moles PO plus 3.4 moles PO.

Reaction charges, details of preparation and the properties of the diols are given in the following table.

TABLE I

| | Water Soluble Precursor Polyols | | |
|---|---|---|---|
| Run no. | 6197-3 | 6197-5 | 6197-15 |
| Charge | | | |
| PEG-600, lb | 7 | 7 | 20 |
| Potassium hydroxide, flaked, g[a] | 17.6 | 17.6 | 15 |
| Propylene oxide, lb ⎫ mixed | 12.4 | 12.4 | 13.4 |
| Ethylene oxide, lb ⎭ | 54.9 | 54.9 | 26.6 |
| Propylene oxide, lb | 8.3 | 8.3 | 6.6 |
| Magnesol 30/40, g | 141 | 141 | 120 |
| Di-t-butyl p-cresol, g | 37.6 | 37.6 | 30.2 |
| Reaction Details | | | |
| Oxide addition time, hr | 5.8 | 5.4 | 5.5 |
| Temperature, °C. | 105-110 | 105-110 | 105-110 |
| Pressure, psig | 50 | 50 | 50 |
| Properties | | | |
| Acid no., mg KOH/g | 0.002 | 0.003 | 0.003 |
| Hydroxyl no., mg KOH/g | 18.2 | 17.3 | 52.2 |
| Water, wt. % | 0.04 | 0.17 | 0.03 |
| Unsaturation, meq/g | 0.025 | 0.033 | 0.005 |
| pH in 10:6 isopropanol-water | 8.1 | 8.0 | 7.7 |
| Color, Pt-Co | 100 | 75 | 45 |
| Sodium, ppm | 0.2 | 0.2 | 0.2 |
| Potassium, ppm | 0.2 | 0.2 | 0.2 |
| Peroxide, ppm | 1.5 | — | 1.44 |
| Viscosity, 100° F., cs | 2568 | 2146 | 235 |
| PO/EO ratio | 24.9/75.1 | 26.8/73.2 | 29.5/70.5 |
| Melting point, °C. | 33 | 32 | liquid |

[a] Added as 45% aqueous solution, dried to water content of less than 0.1 before oxide addition.

The amination of polyol 6197-15 was accomplished using a 1250 ml tubular reactor filled with a nickel oxide-chromium oxide-copper oxide catalyst. The reactor was capped at 20° C. and 2000 psig. The feed rates into the reactor were: polyol 0.8 lb/hr, ammonia 1.6 lb/hr, and hydrogen 76 l/hr. The crude effluent was stripped at 100° C. and 10 mm Hg. The resultant have the following properties:

| Total acetylatables, meg/g | 0.95 |
|---|---|
| Total amine, meg/g | 0.85 |
| Primary amine, meg/g | 0.84 |
| pH | 12.9 |
| Water, wt. % | 0.01 |
| Viscosity, 77° F., cs | 354 |
| Flash point, PM cc, °F. | 480 |
| Color, Pt—Co | 20 |

Having thus described our invention, what is claimed is:

1. A method for preparing a normally-liquid, water-soluble poly(oxyethylene/oxypropylene)-polyamine product having an average molecular weight of about 1,000 to about 8,000 and a functionality of about 2 to about 4 and which comprises charging predetermined amounts of an initiator, ethylene oxide and propylene oxide to a reaction zone in a series of alkoxylation reaction steps with predetermined weight percentages of said reactants, based on said predetermined amounts being charged during each of the alkoxylation steps of the process, each of said alkoxylation reaction steps being conducted under basic substantially anhydrous alkoxylation conditions, said initiator comprising an oxyalkylation susceptible polyhydric alcohol containing about 2 to about 4 hydroxyl groups, having an average molecular of about 200 to about 1000, and also containing oxyethylene groups, and constituting from about 10% to about 60% of the total molecular weight of the water-soluble poly(oxyethylene/oxoypropylene)-polyamine product, said process comprising the steps of:
a. charging said predetermined percentage of said initiator to said reaction zone,
b. alkoxylating said initiator in said reaction zone with said predetermined percentage of ethylene oxide and the first predetermined percentage of propylene oxide to provide a normally liquid intermediate polyol,
c. propoxylating said intermediate polyol with the second predetermined percentage of propylene oxide to provide a normally liquid precursor polyol, and
d. catalytically reductive aminating said precursor polyol in the presence of a reductive amination catalyst in a reaction zone under reductive amination conditions in the presence of ammonia and hydrogen to provide said water-soluble poly(oxyethylene/oxypropylene)-polyamine product, said predetermined percentages, when said initiator contains oxyethylene groups being in about the ranges of:

| | Minimum Weight Percent of | | Maximum Weight Percent of | |
|---|---|---|---|---|
| | Initiator + Ethylene Oxide | Propylene Oxide | Initiator + Ethylene Oxide | Propylene Oxide |
| Intermediate | 60 | 15 | 80 | 25 |
| Precursor | 60 | 20 | 80 | 40 |

-continued

| | Minimum Weight Percent of | | Maximum Weight Percent of | |
|---|---|---|---|---|
| | Initiator − Ethylene Oxide | Propylene Oxide | Initiator + Ethylene Oxide | Propylene Oxide |
| polyol | | | | | said predetermined percentages, when said initiator does not contain oxyethylene groups being in about the ranges of:

| | Minimum Weight Percent of | | Maximum Weight Percent of | |
|---|---|---|---|---|
| | Initiator + Ethylene Oxide | Propylene Oxide | Initiator + Ethylene Oxide | Propylene Oxide |
| Initiator plus Intermediate | 80 | 15 | 60 | 25 |
| Precursor Polyol | 80 | 20 | 60 | 40 | whereby said intermediate polyol will contain all of the said predetermined amount of ethylene oxide and from about 62.5 to about 75 wt.% of the said predetermined amount of propylene oxide, whereby said precursor polyol will contain all of the said predetermined amounts of ethylene oxide and propylene oxide and whereby said normally liquid, water soluble poly(oxyethylene/oxypropylene) polyamine will consist essentially of about 60 to about 80 wt.% of initiator plus ethylene oxide and, correspondingly, from about 40 to about 20 wt.% of propylene oxide.

2. A method as in claim 1 wherein ethylene oxide and the propylene oxide used in the preparation of the intermediate polyol are premixed before being charged to the reaction zone for reaction with said initiator.

3. A method as in claim 1 wherein the initiator is a polyoxyethylene glycol.

4. A method for preparing a normallyliquid, water-soluble poly-(oxyethylene/oxypropylene)-diamine product having an average molecular weight of about 1,000 to about 7,000 which comprises charging predetermined amounts of a polyoxyethylene glycol initiator, ethylene oxide and propylene oxide to an alkoxylation reaction zone in a series of alkoxylation reaction steps with predetermined weight percentages of said reactants, based on said predetermined amounts being charged during each of the alkoxylation steps of the process, each of said alkoxylation reaction steps being conducted under substantially anhydrous basic alkoxylation conditions, said polyoxyethylene glycol initiator having an average molecular of about 200 to about 1000, and constituting from about 10% to about 60% of the total molecular weight of the water-soluble poly-(oxyethylene/oxypropylene)-polyamine product, said process comprising the steps of:
  a. charging said predetermined percentage of said initiator to said reaction zone,
  b. alkoxylating said initiator in said reaction zone with said predetermined percentage of ethylene oxide and the first predetermined percentage of propylene oxide to provide a normally liquid intermediate polyol,
  c. propoxylating said intermediate polyol with said predetermined percentage of propylene oxide to provide a normally liquid precursor polyol, and
  d. catalytically reductively aminating said precursor polyol in the presence of a reductive amination catalyst in a reaction zone under reductive amination conditions in the presence of ammonia and hydrogen to provide said poly(oxyethylene/oxypropylene)-polyamine product said predetermined percentage groups being in about the ranges of:

| | Minimum Weight Percent of | | Maximum Weight Percent of | |
|---|---|---|---|---|
| | Initiator + Ethylene Oxide | Propylene Oxide | Initiator Ethylene Oxide | Propylene Oxide |
| Intermediate | 60 | 15 | 80 | 25 |
| Precursor Polyol | 60 | 20 | 80 | 40 | whereby said intermediate polyol will contain all of the said predetermined amount of ethylene oxide and from about 62.5 to about 75 wt.% of the said predetermined amount of said propylene oxide, whereby said precursor polyol will contain all of the predetermined amounts of ethylene oxide and of propylene oxide and whereby said normally liquid, water soluble poly-(oxyethylene/oxypropylene) diamine will consist essentially of about 60 to about 80 wt.% of initiator plus said ethylene oxide and, correspondingly, about 40 to about 20 wt.% of said propylene oxide.

5. A method as in claim 4 wherein ethylene oxide and the propylene oxide used in the preparation of the intermediate polyol are premixed before being charged to the reaction zone for reaction with said initiator.

6. A normally-liquid, water-soluble poly(oxyethylene/oxypropylene)-polyamine product having an average molecular weight of about 1,000 to about 8,000 and a functionality of about 2 to about 4, said polyamine having been prepared by charging predetermined amounts of an initiator, ethylene oxide and propylene oxide to an alkoxylation reaction zone in a series of alkoxylation reaction steps with predetermined weight percentages of said reactants, based on said predetermined amounts charged during each of the alkoxylation steps of the process, each of said alkoxylation reaction steps being conducted under substantially anhydrous basic alkoxylation conditions, said initiator comprising an oxyalkylation susceptible polyhydric alcohol containing about 2 to about 4 hydroxyl groups and having an average molecular of about 200 to about 1000, and also containing oxyethylene groups, and constituting from about 10% to about 60% of the total molecular weight of the water-soluble poly(oxyethylene/oxypropylene)-polyamine product, said process comprising the steps of:
  a. charging said predetermined percentage of said initiator to said reaction zone,
  b. alkoxylating said initiator in said reaction zone with said predetermined percentage of ethylene oxide and the first predetermined percentage of propylene oxide to provide a normally liquid intermediate polyol, c. propoxylating said intermediate polyol with the second predetermined percentage of propylene oxide to provide a normally liquid precursor polyol, and d. catalytically reductively aminating said precursor polyol in the presence of a reductive amination catalyst in a reaction zone under reductive amination conditions in the presence of ammonia and hydrogen to provide said water-soluble poly(oxyethylene/oxypropylene)-polyamine product, said predetermined percentages, when said initiator contains oxyethylene groups being in about the ranges

|  | Minimum Weight Percent of | | Maximum Weight Percent of | |
| --- | --- | --- | --- | --- |
|  | Initiator + Ethylene Oxide | Propylene Oxide | Initiator + Ethylene Oxide | Propylene Oxide |
| Intermediate | 60 | 15 | 80 | 25 |
| Precursor Polyol | 60 | 20 | 80 | 40 | said predetermined percentages, when said initiator does not contain oxyethylene groups being in about the ranges of:

|  | Minimum Weight Percent of | | Maximum Weight Percent of | |
| --- | --- | --- | --- | --- |
|  | Initiator + Ethylene Oxide | Propylene Oxide | Initiator + Ethylene Oxide | Propylene Oxide |
| Initiator plus Intermediate | 80 | 15 | 60 | 25 |
| Precursor Polyol | 80 | 20 | 60 | 40 | whereby said intermediate polyol will contain all of the said predetermined amount of ethylene oxide and from about 62.5 to about 75 wt.% of the said predetermined amount of propylene oxide, whereby said precursor polyol will contain all of the said predetermined amounts of ethylene oxide and of propylene oxide and whereby said normally liquid, water soluble poly(oxyethylene/oxypropylene) polyamine will consist essentially of about 60 to about 80 wt.% of initiator plus ethylene oxide and, correspondingly, from about 40 to about 20 wt.% of propylene oxide.

7. A polyamine as in claim 6 wherein the ethylene oxide and the propylene oxide used in the preparation of the intermediate polyol are premixed before being charged to the reaction zone for reaction with said initiator.

8. A polyamine as in claim 6 wherein the initiator is a polyoxyethylene glycol.

9. A normally-liquid, water-soluble poly(oxyethylene/oxypropylene)-diamine product having an average molecular weight of about 1,000 to 8,000, said diamine having been prepared by the method of charging predetermined amounts of a polyoxyethylene glycol initiator, ethylene oxide and propylene oxide to an alkoxylation reaction zone in a series of alkoxylation reaction steps with predetermined weight percentages of said reactants, based on said predetermined amounts being charged during each of the alkoxylation steps of the alkoxylation process, each of said alkoxylation reaction steps being conducted under substantially anhydrous basic alkoxylation conditions, said polyoxyethylene glycol initiator having an average molecular of about 200 to about 1000, and constituting from about 10% to about 60% of the total molecular weight of the water-soluble poly-(oxyethylene/oxypropylene)polyamine product, said method consisting essentially of the steps of:

a. charging said predetermined percentage of said initiator to said alkoylation reaction zone, b. alkoxylating said initiator in said reaction zone with said predetermined percentage of ethylene oxide and the first predetermined percentage of propylene oxide to provide a normally liquid intermediate polyol, c. propoxylating said intermediate polyol with the second predetermined percentage of propylene oxide to provide a normally liquid precursor polyol, and d. catalytically reductively aminating said precursor polyol in the presence of a reductive amination catalyst in a reaction zone under reductive amination conditions in the presence of ammonia and hydrogen to provide said diamine product, said predetermined percentage groups being in about the ranges of:

|  | Minimum Weight Percent of | | Maximum Weight Percent of | |
| --- | --- | --- | --- | --- |
|  | Initiator + Ethylene Oxide | Propylene Oxide | Initiator + Ethylene Oxide | Propylene Oxide |
| Intermediate | 60 | 15 | 80 | 25 |
| Precursor Polyol | 60 | 20 | 80 | 40 | whereby said intermediate polyol will contain all of the said predetermined amount of ethylene oxide and from about 62.5 to about 75 wt.% of the said predetermined amount of said propylene oxide, whereby said precursor polyol will contain all of the predetermined amounts of ethylene oxide and of propylene oxide and whereby said normally liquid, water soluble poly-(oxyethylene/oxypropylene) diamine will consist essentially of about 60 to about 80 wt.% of initiator plus said ethylene oxide and, correspondingly, about 40 to about 20 wt.% of said propylene oxide.

10. A diamine as in claim 9 wherein ethylene oxide and the propylene oxide used in the preparation of the intermediate polyol are premixed before being charged to the reaction zone for reaction with said initiator.

11. A method for preparing a normally liquid, water-soluble poly(oxyethylene/oxypropylene)-diamine product having an average molecular weight of about 1,000 to about 8,000, and consisting essentially of from about 60 to about 80 wt.% of initiator plus ethylene oxide and, correspondingly, about 40 to about 20 wt.% of propylene oxide which consists essentially of the steps of:

a) preparing a normally liquid intermediate glycol by alkoxylating a glycol initiator consisting essentially of a polyoxyethylene glycol having a molecular weight of about 200 to about 1000 in an alkoxylation reaction zone under basic substantially anhydrous alkoxylation reaction conditions with all of the required amount of ethylene oxide and from about 62.5 to about 75 wt.% of the required amount of propylene oxide.

b) propoxylating said intermediate glycol in a propxylation reaction zone under basic substantially anhydrous propoxylation conditions with the remainder of the said required amount of propylene oxide to provide a normally liquid precursor glycol and c) catalytically reductively aminating said precursor polyol in the presence of a reductive amination catalyst, hydrogen and ammonia in a reductive amination reaction zone under reductive amination conditions to provide said normally liquid, water-soluble poly(oxyethyelne/ oxypropylene)-diamine product.

12. A method as in claim 11 wherein the initiator consists essentially of a polyoxyethyelene glycol having an average molecular weight of about 600.

13. A normally-liquid, water-soluble poly(oxyethylene/oxypropylene)-diamine product having an average molecular weight of about 1,000 to about 8,000, and consisting essentially of from about 60 to about 80 wt.% of initiator plus ethylene oxide and, correspondingly, about 40 to about 20 wt.% of propylene oxide, said diamine having been prepared by a process consisting essentially of the steps of:

a) preparing a normally liquid intermediate glycol by alkoxylating a glycol initiator consisting essentially of a polyoxyethylene glycol having a molecular weight of about 200 to about 1000 in an alkoxylation reaction zone under basic substantially anhydrous alkoxylation reaction conditions with all of the required amount of ethylene oxide and from about 62.5 to about 75 wt.% of the required amount of propylene oxide, b) propoxylating said intermediate glycol in a propoxylation reaction zone under basic substantially anhydrous propoxylation conditions with the remainder of the said required amount of propylene oxide to provide a normally liquid precursor glycol and c) catalytically reductively aminating said precursor polyol in the presence of a reductive amination catalyst, hydrogen and ammonia in a reductive amination reaction zone under reductive amination conditions to provide said normally liquid, water-soluble poly(oxyethylene/oxypropylene)-diamine product.

14. A polyamine as in claim 13 wherein the initiator consists essentially of a polyoxyethylene glycol having an average molecular weight of about 600.

* * * * *